United States Patent [19]

Ritchey et al.

[11] Patent Number: 4,647,452

[45] Date of Patent: Mar. 3, 1987

[54] ORAL COMPOSITIONS OF SALICYLAMIDES AND ZINC SALTS FOR THE SYNERGISTIC INHIBITION OF DENTAL PLAQUE

[75] Inventors: Thomas W. Ritchey, Norwood; Erwin Sharpe, West New York, both of N.J.

[73] Assignee: Lever Brothers Company, New York, N.Y.

[21] Appl. No.: 796,347

[22] Filed: Nov. 8, 1985

[51] Int. Cl.[4] .................. A61K 7/22; A61K 33/30
[52] U.S. Cl. ................... 424/54; 424/145; 514/835
[58] Field of Search ............ 424/49, 54, 145; 514/835

[56] References Cited

U.S. PATENT DOCUMENTS

| | | |
|---|---|---|
| 4,022,880 | 5/1977 | Vinson et al. .................. 424/49 |
| 4,100,269 | 7/1978 | Pader .............................. 424/49 |
| 4,146,607 | 3/1979 | Ritchey .......................... 424/54 |
| 4,154,815 | 5/1979 | Pader .............................. 424/50 |
| 4,287,191 | 9/1981 | Coburn et al. ............... 424/230 |
| 4,339,432 | 7/1982 | Ritchey et al. ................. 424/54 |
| 4,358,443 | 11/1982 | Coburn et al. ............... 424/230 |
| 4,522,806 | 6/1985 | Muhlemann et al. .......... 424/52 |

FOREIGN PATENT DOCUMENTS

| | | |
|---|---|---|
| 961412 | 1/1975 | Canada .......................... 424/54 |
| 1427290 | 6/1966 | France ........................... 424/54 |

*Primary Examiner*—Douglas W. Robinson
*Attorney, Agent, or Firm*—Milton L. Honig; James J. Farrell

[57] ABSTRACT

A composition and method for retarding plaque are disclosed. The composition comprises a mixture of a zinc salt with a non-ring halogenated aromatic salicylamide of a specified structure.

8 Claims, No Drawings

ORAL COMPOSITIONS OF SALICYLAMIDES AND ZINC SALTS FOR THE SYNERGISTIC INHIBITION OF DENTAL PLAQUE

BACKGROUND OF THE INVENTION

1. Field of the Invention

This invention relates to oral compositions and their use in a method for controlling dental plaque.

2. The Prior Art

Dental plaque forms as a film on teeth. It is a dense microbial layer formed as a product of microbial growth. The closely matted microorganisms in plaque are embedded in a proteinaceous matrix of uncertain origin that is generally considered to be at least partially salivary. The microorganisms involved are mainly coccoidal, this is especially true in early plaque which in the mouths of some persons change to filamentous organisms after a few days.

It is believed that dental plaque precedes calculus. Also, it is generally accepted by dental experts that clinical supra-gingival calculus (tartar) is a type of dental plaque which is mineralized with a formation of a calcium phosphate crystalline-structure. It will be apparent therefore that the incidence of calculus formation can be reduced by employing dental compositions which reduce or prevent the deposition of plaque.

Dental plaque has been observed to form following dental prophylaxis. This plaque was attributed to bacteria acquired from the saliva where they had resided and remained unaffected by the prophylaxis treatment. Plaque may form on any part of the tooth surface. It is found particularly at the gingival margin, and on the surface of dental calculus. Plaque, like calculus, is considered to be a prime causative factor in peridontal disease. Gingivitis and other types of gingival disease arise when plaque is not controlled.

A wide variety of chemical agents have been suggested to retard plaque formation and the resulting plaque diseases. Mechanical removal of plaque is attempted with oral hygiene measures, but average toothbrushing only partially results in plaque removal. Therefore, the additional use of chemical antibacterials inhibiting plaque formation in inaccessible dental areas is indicated. Germicides which have been proposed include phenolic compounds, halogenated bis-phenols (e.g. hexachlorophene), organic mercurials, hydroxyquinolines, iodine esters of hydroxybenzoic acids, chloramine T, and surface active compounds (detergents) among others. These germicides are excellent laboratory disinfectants but are relatively poor in vivo plaque inhibitors.

The antiplaque properties of metal ions were mentioned as early as 1940 (Hanke, M. T.: "Studies on the local factors in dental caries. I. Destruction of plaque and retardation of bacterial growth in the oral cavity". JADA 27, 379, 1940). U.S. Pat. No. 1,593,485 refers to zinc phenolsulfonate as a bactericide. The use of zinc oxide or zinc phosphate for the stabilization of dental creams is described in U.S. Pat. No. 3,622,662. Zinc oxide and zinc sulphate are described in U.S. Pat. No. 3,624,199 for the same purpose. Effervescent antiplaque tablets containing zinc chloride are described in U.S. Pat. No. 3,888,976.

Antiplaque and anticalculus effects have been claimed in U.S. Pat. No. 4,146,607 for zinc ions combined with tetradecylamine. U.S. Pat. No. 4,339,432 discloses mouthwashes combining zinc and glycine. Combinations of zinc salts and enzymes are reported for their oral activity in U.S. Pat. No. 4,082,841.

Antiplaque effects of oral rinses containing zinc salts and antibacterials have been reported in U.S. Pat. No. 4,022,880. Among the antibacterials listed in this patent are halogenated salicylanilides, halogenated carbanilides, halogenated bisphenols, alkylbenzoyl acrylates, halogenated anilides, quaternary ammonium compounds, thiuram sulfides, dithiocarbamates, antibiotics, halogenated diphenol ethers, halogenated anilides of thiophene carboxylic acids, and chlorhexidines. U.S. Pat. No. 4,522,806 discloses the antiplaque activity of zinc salts in combination with hexetidine.

As may be noted from the foregoing description of the prior art, zinc salts and combinations of these salts with antibacterials and other actives have been shown to be inhibitors of dental plaque. There are, however, taste, formulation and safety difficulties associated with zinc salts and many of their coactives. It has also been found desirable to obtain antiplaque compositions with increased efficiency.

Accordingly, it is an object of the present invention to provide an oral composition of improved effectiveness against dental plaque.

Another object of this invention is to provide antiplaque compositions of improved taste and better formulation compatibility.

A further object of this invention is to provide a method for reducing plaque and the resultant calculus formed in the oral cavity.

SUMMARY OF THE INVENTION

An oral composition is provided comprising:

(i) from about 0.001 to 10% of a salicylamide having the formula:

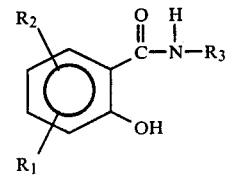

I wherein the lipophilicity imparting substituents —$R_1$ and —$R_2$ which impart an octanol/water distribution function of about 3.0 to about 10 to said compound are —H, normal or branched chain or cyclic or fused ring polycyclic or non-fused ring polycyclic alkyl, alkenyl, alkynyl, aryl or heteroaryl groups optionally containing further substituents thereon, said —$R_1$ and —$R_2$ substituents comprising up to about 30 carbon atoms when taken together either attached directly to the phenyl ring provided with an amido and a hydroxyl group in an ortho orientation with respect to each other or attached to said phenyl ring through a

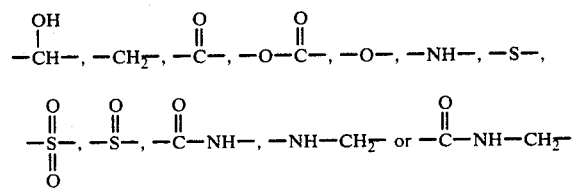

group with the proviso that —$R_1$ and —$R_2$ are not both —H and wherein —$R_3$ is selected from the group consisting of thiazol-2-yl, benzothiazol-2-yl and R$_4$-substituted phenyl wherein R$_4$ is selected from the group consisting of —OH, —COOH, the tautomeric pair

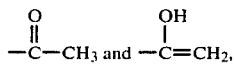

—CH$_2$COOH, —COOCH$_3$, —COOC$_2$H$_5$, —CH$_2$COOCH$_3$, —CH$_2$COOC$_2$H$_5$, —NO$_2$, and CX$_1$X$_2$X$_3$ wherein X$_1$, X$_2$ and X$_3$ are halogen atoms, with halogen atoms directly attached to any aromatic ring being absent in said compounds; and (ii) from about 0.001 to about 10% of a physiologically acceptable zinc salt.

Particularly preferred salicylamides covered by the general formula are:

(a) R$_1$ is H, R$_2$ is 5,n-octanoyl, and R$_3$ is p-trifluoromethylphenyl;

(b) R$_1$ is H, R$_2$ is 5,n-decanoyl, and R$_3$ is benzothiazol-2-yl and (c) R$_1$ is H, R$_2$ is 5,n-decanoyl, the —OH group is replaced by acryloyloxy and R$_3$ is p-nitrophenyl.

DETAILED DESCRIPTION OF THE INVENTION

It has now been discovered that dental plaque and calculus can be greatly reduced by contacting the teeth with a combination of zinc ions and certain salicylamides which are non-halogenated on their aromatic rings. Salicylamides are known for their analgesic and anti-inflammatory properties and have been recognized as being effective antiplaque agents. See, Batista, A. J., "Salicylanilides: Design, Synthesis, and In Vitro Evaluation as Inhibitors of Dental Plaque-Forming Microorganisms", Ph.D. Dissertation, State University of New York at Buffalo, 1980; U.S. Pat. No. 4,358,443; and U.S. Pat. No. 4,287,191. A combination of certain salicylamides identified by formula I when combined with zinc ions were surprisingly found to provide substantially more antiplaque activity than would be expected from the mere additive effects of both antiplaque agents individually.

In the Formula I shown above, alkyl can be straight or branched chain, e.g., n-octyl, n-decyl or tert-butyl; cycloalkyl can be monocyclic, e.g.,

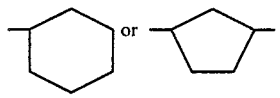

fused polycyclic, e.g.,

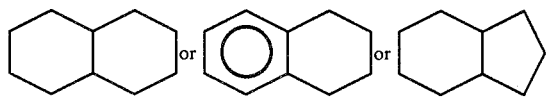

or non-fused polycyclic, e.g.,

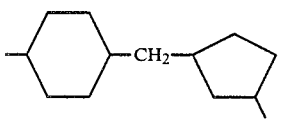

alkenyl can be, e.g., CH$_2$=CH$_2$—(CH$_2$)$_n$— where n is an integer or CH$_3$—(CH$_2$)$_n$CH=CH(CH$_2$)$_m$— where n and m are each either zero or an integer it being understood that one or more double bonds may be included in the formula;

alkynyl can be, e.g., HC≡C— or CH$_3$(CH$_2$)$_n$—C≡C—(CH$_2$)$_m$— where m and n are each zero or an integer it being understood that one or more triple bonds may be included in the formula:

aryl can be mono or polycyclic, e.g.,

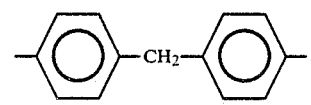

and heteroaryl can be mono or polycyclic and can contain 1,2,3 or more heteroatoms, e.g., N, O or S, e.g.,

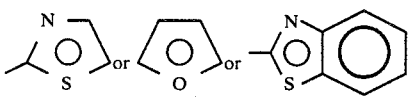

Each of the respective groups can bear one or more substituents such that —R$_1$ and —R$_2$ taken together contain collectively up to about 30 carbon atoms and —R$_3$ contains up to about 25 carbon atoms. It will therefore be understood that the examples given are only illustrative and not limitative of the invention.

The preferred salicylamides of Formula I have an octanol/water distribution coefficient greater than 3.0 and the substituted moieties —R$_4$ in the phenyl ring of the secondary amido ligand (when the —R$_3$ ligand takes the form —PhR$_4$, pH being a phenyl ring) have a combined overall electron withdrawing effect on said phenyl ring.

The term "distribution coefficient" of a composition as used herein is the log$_{10}$ P where P is the ratio of the concentration of the composition in octanol to the concentration of the composition in water in a two phase octanol-water system. A distribution coefficient of, e.g., 5 therefore means that the ratio of the concentration of the compound in octanol to the concentration in water is $10^5$ or 100,000 to 1. The distribution coefficient is a measure of the lipophilic character of the compound. The preferred compounds of Formula I are lipophilic as indicated by a distribution coefficient of greater than about 3.0. The distribution coefficient is however usually less than 10.

The preferred compounds of Formula I are those of the structure shown below:

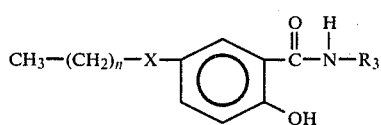

wherein n is an intger, preferably from 3 to 14, R$_3$ is as defined above and X is

or a covalent bond joining the alkyl group to the phenyl ring. When —$R_3$ is an $R_4$— substituted benzene ring, $R_4$— preferably is para —$NO_2$, meta —$COOC_2H_5$ or meta or para —$CF_3$.

Of the preferred compounds, especially preferred are those wherein:

(a) n is 8, X is

and —$R_3$ is a para-nitrophenyl, (hereinafter called AN-10), (b) n is 6, X is

and —$R_3$ is a para-trifluoromethylphenyl (hereinafter called APCF3-8), (c) n is 6, X is

and —$R_3$ is a meta-trifluoromethylphenyl (hereinafter called AMCF3-8), (d) n is 5, X is a covalent bond and —$R_3$ is a para-nitrophenyl (hereinafter called SAN-6), (e) n is 3, X is a covalent bond and —$R_3$ is a metatrifluoromethylphenyl (hereinafter called S-4-F), (f) n is 7, X is

and —$R_3$ is meta-carbethoxyphenyl (hereinafter called ACBXE-9), (g) n is 8, X is

and —$R_3$ is benzothiazol-2-yl (hereinafter called ABC-4), and (h) n is 14, X is

and —$R_3$ is thiazol-2-yl (hereinafter called RV-19), (i) n is 8, X is

—$R_3$ is a para-nitrophenyl and the —OH group of Formula I is replaced with a $CH_2$=CH—COO— group (hereinafter called ACN-10).

The salicylamides of Formula I are known and described in existing literature. A representative, although not the only available or conceivable method of synthesis, is disclosed in U.S. Pat. No. 4,287,191 and pending U.S. patent application Ser. No. 525,916 (Ritchey), both of which are herein incorporated by reference.

In general, salicylamides can be prepared by reacting a lower alkyl ($R_a$) salicylate ester with an acyl chloride ($R_x$COCl) in the presence of a Lewis acid to form an ester of a 5-acylsalicylic acid. The 5-acylsalicylic acid ester is then hydrolyzed and the resulting free acid is reacted with a substituted amine or aniline $H_2N$—$R_3$ to form the 5-acylsalicylamide. The term "lower alkyl" as used herein means alkyl of from 1 through 4 carbon atoms. $R_x$ is n—$C_7$ in the case of APCF3-8 and AMCF3-8. It is n—$C_9$ in the case of AN-10. It is n—$C_8$, n—$C_9$ and n—$C_{15}$ in the cases involving ACBXE-9, ABC-4 and RV-19 respectively. In the cases of SAN-6 and S-4-F, the Friedel-Crafts acylation step is replaced by a Friedel-Crafts alkylation process by substituting the acid chloride $R_x$—CO—Cl by a normal alkyl halide $R_x$Cl. In the cases of SAN-6 and S-4-F which are prepared by way of the Friedel-Crafts alkylation initial step, $R_x$ is $C_6$ and $C_4$, respectively. $R_3$ is a substituted benzene ring or a thiazole or a benzothiazole ring. In the case of a substituted benzene ring, the substituents may be —$NO_2$ in a para position or —$COOC_2H_5$ in a meta position or —$CF_3$ in either a para or a meta position. When $R_3$ is one of the two heterocyclic attachments mentioned above, the linking thereof to the secondary amido nitrogen atom occurs through the No. 2 carbon atom of the heterocyclic attachment. ACN-10 is, as already noted above, an acrylic acid derivative of AN-10 wherein the 2-hydroxy group of AN-10 is replaced by the $CH_2$=CH—COO—group. Such replacement is accomplished by the esterification of AN-10 in the manner generally employed for the esterification of phenols. Thus, esterification of AN-10 with acryloyl chloride in pyridine or other base results in the esterified product, i.e., ACN-10.

As a usual procedure, the 5-acyl or 5-alkyl salicylic acid precursor is prepared in a medium or reaction solvent which is customarily considered suitable for the conductance of a Friedel-Crafts acylation or alkylation with optimal yield, minimal side reactions, non-onerous reaction conditions and minimal reaction time. A preferred reaction solvent is carbon disulfide. Anhydrous aluminum chloride or other Lewis acid is initially added to the carbon disulfide and the mixture is cooled, e.g. with ice. A solution of the alkyl salicylate ester, e.g. methyl salicylate, and an acyl halide, e.g. a chloride (or an alkyl halide as applicable) in carbon disulfide or other reaction solvent is then slowly added and the temperature is maintained below about 10° C. After completion of reaction which may take as long as 24 hours, the reaction mass is poured into ice water and the mixture is then extracted with a suitable solvent such as ether. The ether or other extract is washed with water and then dried over anhydrous sodium sulfate. Thereafter, the ether or other solvent is evaporated in vacuo. The resulting solid residue is dissolved in a suitable solvent such as ethanol and treated with a solution of an alkali metal hydroxide, e.g. 2N NaOH solution. After heating to a temperature of between about 80° to 120° C., e.g. on a steam bath, the mass is cooled and acidified with a suitable acid such as HCl to a pH of about 1 to precipitate the product. Recrystallization from ethanol gives purified 5-acylsalicylic acid or 5-alkylsalicylic acid, depending on whether an acid halide or an alkyl halide was the initial Friedel-Crafts reactant.

The 5-acyl or 5-alkyl salicylic acid is reacted with the appropriate substituted aniline or other amine, e.g. p-nitroaniline in the case of AN-10, in a suitable reaction solvent such as chlorobenzene. Desirably the 5-acyl or 5-alkylsalicylic acid is pre-reacted with phosphorus trichloride in the solvent at a suitable temperature, e.g. between about 55° C. and about 80° C. The reaction time is usually between about one and about five hours. The solution is then cooled and the appropriate substituted aniline or heterocyclic amine, e.g. p-nitroaniline is then added and the solution is again heated to a suitable temperature, e.g. between about 55° C. and about 80° C. as previously described for about one to about five hours and is then refluxed until the reaction is complete, e.g. for about 24 hours. The solvent is then removed in vacuo and the residue is purified by recrystallization from a mixture of a suitable solvent such as a mixture of ethanol and water. The resulting product is an amido compound of the invention.

Detailed descriptions of the methods of synthesis of 5-n-decanoylsalicylic acid and of AN-10 therefrom are given in Examples 1 and 2 of U.S. Pat. No. 4,287,191.

Methods of synthesis of the other preferred compounds of the invention, namely APCF3-8, AMCF3-8, SAN-6, S-4-F, ACBXE-9, ABC-4 and RV-19 follow naturally from the method of synthesis described for AN-10 with appropriate substitution of the respective reactants. ACN-10 is prepared, as already noted above, from AN-10 by esterification of the phenolic —OH group of AN-10 with acryloyl chloride in pyridine.

Salicylamides of Formula I may be present from about 0.001% to about 10% by weight of the total oral composition. Preferably, the concentration ranges from about 0.01 to about 2%, more preferably from about 0.05 to about 1.5% and most preferably from about 0.1 to about 1% by weight of the total composition.

Zinc ions may be furnished by any pharmaceutically acceptable zinc salt having sufficient solubility in the solvent medium carrier to provide an effective level of zinc ions, i.e. zinc cations, at the site of action of the zinc ion. The remainder of the molecule of the zinc salt may be inert for antiplaque and anticalculus purposes.

By "zinc ion" is meant the zinc-atom portion of the molecule of a zinc compound in the solid or undissociated state, and capable of being dissociated into simple or complex zinc ions at temperatures of about 37° C., as well as to simple or complex zinc ions formed in an aqueous medium such as a mouthwash or oral salivary secretions.

The term "pharmaceutically acceptable" used herein with reference to zinc compounds, is applicable to those compounds which, under the conditions of use and in the compositions set forth herein, are safe and organoleptically tolerable in the oral cavity, and have no significant side effects either orally or systemically.

In mouthwashes, it is preferred to use the more soluble zinc salts, e.g., those having a solubility in water at 20° C. of the equivalent of at least about one gram of Zn per 100 ml. of water. A particularly preferred zinc compound is zinc phenolsulfonate, because it is virtually insensitive to pH change, for example to the adjustment of the pH of a mouthwash to near neutrality, with respect to hydrolysis and precipitation.

Zinc compounds having a solubility in water as low as the equivalent of about $1 \times 10^{-8}\%$ zinc may be used, as well as those having solubilities ranging from the aforesaid level up to that of the most soluble zinc compounds, for example that of zinc bromide, which is about 447 grams (equivalent to about 130 grams $Zn^{++}$) per 100 ml at 29° C.

The solubilities and zinc contents of zinc compounds having utility in accordance with the instant invention may be derived from data readily obtainable in the literature.

Examples of the compounds that may be employed are zinc salts of the following organic and inorganic anions; acetate, benzoate, borate, bromide, carbonate, citrate, chloride, fluoride, glycinate, hexafluorosilicate, dl-lactate trihydrate, phenolsulfonate, silicate, alkanoates having 8 to 18 carbon atoms, sulfate, tannate and titanate.

The zinc salts, according to the instant invention, will generally be present in the oral composition in an amount of from about 0.001% to about 10%. Preferably, they will be present from about 0.01 to about 2%, more preferably from about 0.05 to about 2%, most preferably from about 0.1 to about 1.5%. In the case of mouthwash products, the zinc salt may be added at a level of about 0.04% to about 0.7% by weight of soluble zinc ion, with 0.04% being the approximate minimum active concentration and 0.7% being the approximate concentration at which astringency becomes objectionable. The preferred concentration of zinc ion in a mouthwash is 0.1%–0.3%, and 0.2% to 3% in a toothpaste.

The balance of the oral composition in accordance with the present invention will consist of the usual carrier media and other desired substances consistent with the form it is in. For example, where the oral composition contemplated is a mouthwash, the balance of the preparation will usually contain water, or water and a mono- or polyhydric alcohol such as ethanol, glycerol, or sorbitol, and optionally, flavoring substances and foaming agents. Glycerol and sorbitol are also useful as aids in sweetening the product. Surfactants and/or suspending agents are usually present in mouthwashes as solubilizers for essential flavoring oils. The customary solubilizers for this purpose are the sorbitan fatty acid esters, the polyoxyethylene derivatives thereof, and polyoxyethylene fatty acid ethers.

When the oral composition is in the form of a toothpaste, there may be present polishing agents, humectants, bodying agents, flavoring substances, sweetening substances, foaming agents, etc. It will be understood that the polishing agents and other components suitable for use in the toothpastes of the invention must be compatible with the zinc compounds and salicylamides.

Among the suitable inorganic polishing agents useful in accordance with the invention are the silica xerogels and silica aerogels manufactured by the Davison Chemical Division of W. R. Grace and Company, for example those available under the trade names of Syloid 63 and Syloid 65 (xerogels), and Syloid 244 (aerogels). The xerogels are synthetic, aggregated, amorphous, highly porous silicas having generally a mean particle diameter of about 4 to 10 microns. The aerogel Syloid 244 has a mean particle diameter of about 3 microns and is more porous than the xerogels. Also useful are other polishing agents disclosed hereinafter.

The polishing agent should be in the form of fine particles, as is well known in the art. Preferably, the particles should be of such size that at least 40% pass through a 325 mesh screen, and at least 90% pass through a 20 mesh screen. The finer particles within this size range are preferred, particularly a size distribution such that all the particles pass through a 20 mesh screen; more than 90% pass through a 100 mesh screen; more than 80% pass through a 200 mesh screen; and more than 40% pass through a 325 mesh screen. Especially preferred are the finer particles having a mean particle diameter of about 3 to about 44 microns.

Other substances proposed as dental abrasives include various abrasive materials such as silica embedded in protective plastic particles, chalks, metaphosphates, pyrophosphates, and dicalcium phosphate dihydrate.

Polishing agents will be present in the toothpastes of the invention over the broad range of about 1% to 70%, preferably 10% to 60%, and typically from about 20% to 50%. In a tooth powder, the polishing agent will be present over the range of about 50% to 99%, preferably from about 70% to 95%, and typically from about 90% to about 95%.

The toothpastes will usually contain compatible bodying agents such as gum Karaya, gum Tragacanth, starch, sodium carboxymethylcellulose, Irish moss, gum arabic, sodium carboxymethylhydroxyethylcellulose, polyvinylpyrrolidone, etc. When present, these will usually be at levels of from about 0.5% to about 3%, preferably from about 0.8% to about 1.5%.

Humectants are desirable in a toothpaste to provide smooth texture and flowability. These will usually be such compounds as glucose, honey, glycerol, propylene glycol, sorbitol, polyethylene glycol 400, and other polyhydric alcohols, and may be present in the composition in amounts of up to about 80% by weight.

Other adjuvants may be present, such as fluorides, chlorphyll compounds, flavoring substances, saccharin, aspartame, urea, ammonium compounds, alcohol, mineral oil, and foaming agents or detergents, such as sodium lauryl sulfate, dodecanesulfonate, acyl taurines, acyl isethionates, etc., depending upon the form of the product.

Chewing gum compositions are also within the scope of this invention. A chewing gum medium normally comprises a gum base and common flavoring materials used in the field. The flavoring materials are present at a level of about 0.01–2.0% of the final chewing gum composition. The base is a chewable plastic gum material such as natural rubber, chickle, polyvinyl acetate, ester gum, coumarone resin and paraffin wax. The gum base is typically made from a mixture of two or more plastic gum materials to achieve a preferred degree of plasticity for chewing. Optionally, a binder or a softener may be used as well as sweetening agents. Lozenges may also be made containing the synergistic combination of this invention.

TEST PROCEDURE FOR DETERMINING ANTIPLAQUE ACTIVITY

The in vitro test used for examining the effects of chemotherapeutic agents on plaque was reported in the "Journal of Dental Research", Vol. 55, February 1976, page B286, by R. T. Evans, P. J. Baker, R. A. Coburn and R. J. Genco. This assay system for producing artificial plaque was developed to rapidly screen antiplaque agents under conditions which simulate those found in the oral cavity. Evans et al. found that effective dosages in the in vitro assay correlated with results of previously published clinical studies. The assay gives reproducible, quantitative results and has the ability to distinguish between antibacterial agents which are clinically effective or non-effective as plaque inhibitors.

The in vitro plaque was formed at 37° C. on uniformly-sized aluminum plummets which were first coated with saliva. The plummets were then placed in a growth medium inoculated with clinical plaque samples. After seven hours the plummets were suspended overnight in a 25% saliva mixture. On the second day, the plummets were immersed in a 50% saliva—50% test compound mixture for one minute, placed in the growth medium for seven hours, retreated with the test mixture and suspended in 25% saliva overnight. The plummets were treated again on the third day and incubated in the growth medium for three hours. The plaques were removed from the plummets by sonication into approximately six milliliters of buffer and quantitated by optical density (O.D.) in a Beckman DU at 570 mm.

A test compound showed antiplaque activity if the O.D. (plaque mass) was reduced from the control plaques treated with water. Positive controls were included to determine relative activity. Comparisons of antiplaque activity were then made within a given experiment. At least five replicas per compound were examined.

The following Examples will more fully illustrate the embodiments of this invention. All parts and proportions referred to herein and in the appended claims are by weight unless otherwise noted.

EXAMPLE 1

The following Example illustrates the interactive effective of three different types of salicylamide (i.e. AN-10, APCF3-8 and ACN-10) with zinc salts in an aqueous media. Samples 1–4 and 5–12 of the Table are separated into Sets A and B because the comparative placebos and test conditions were slightly varied. As a result, each of the two placebos exhibited a different response. Samples within each group were compared to their respective placebo values. In Table I, the placebo of set B consisted of 25% ethanol, 25% propylene glycol, 0.5% Pluronic 84 (an ethylene oxide-propylene oxide polymer sold by Rohm & Haas Company) and 0.4% glycine with the balance water. The placebo of set A did not contain glycine and the Pluronic 84 was substituted with 1.5% Tween 20®, a trademark of ICI, Americas, representing sorbitan monolaurate ethoxylated with 20 moles ethylene oxide.

It was found that both zinc chloride and zinc phenol sulfonate provided about 5% plaque reduction. This finding is supported by the results of clinicals reported in the scientific literature.

In set A, the salicylamide AN-10 reduced plaque by about 21%. The combination of AN-10 and zinc phenolsulfonate, however, reduced plaque by 60%. It should be noted that the halogenated congener of AN-10, 3,4',5-tribromo salicylanilide (TBS) can reduce plaque by about 20% but the combination of zinc phenol sulfonate and TBS reduces plaque by only about 35%.

Set B of Table I compares various salicylamides in combination with zinc chloride. Relative to the placebo of set B, AN-10 alone appeared to have a greater plaque reduction effect than relative to the placebo of set B. Nonetheless, the combination of AN-10 with zinc chloride gave a plaque reduction of 68%, which is greater than the sum of the separate actives. Combinations of zinc chloride with APCF3-8 and ACN-10 provided significantly more plaque reduction than would have been expected from a merely additive combination of salicylamide and zinc salt.

TABLE I

| Set | Sample | Salicylamide Type | Wt. % Salicylamide | Zinc Salt Type | Wt. % Zn Salt | Average Optical Density | Standard Deviation | % Plaque Reduction |
|---|---|---|---|---|---|---|---|---|
| A. | 1 | | | Placebo | | 0.190 | 0.009 | (reference) |
| | 2 | — | | Phenolsulfonate | 0.66 | 0.180 | 0.011 | 5.3 |
| | 3 | AN-10 | 0.05 | — | — | 0.150 | 0.019 | 21.1 |
| | 4 | AN-10 | 0.05 | Phenolsulfonate | 0.66 | 0.076 | 0.010 | 60.0 |
| B. | 5 | | | Placebo | | 1.556 | 0.086 | (reference) |
| | 6 | — | — | Chloride | 0.2 | 1.468 | 0.081 | 5.7 |
| | 7 | AN-10 | 0.05 | — | — | 0.632 | 0.109 | 59.4 |
| | 8 | AN-10 | 0.05 | Chloride | 0.2 | 0.498 | 0.042 | 68.0 |
| | 9 | APCF3-8 | 0.05 | — | 13 | 0.613 | 0.202 | 60.6 |
| | 10 | APCF3-8 | 0.05 | Chloride | 0.2 | 0.310 | 0.080 | 80.1 |
| | 11 | ACN-10 | 0.025 | — | — | 0.733 | 0.110 | 52.9 |
| | 12 | ACN-10 | 0.025 | Chloride | 0.2 | 0.204 | 0.065 | 87.5 |

EXAMPLE 2

The following Example illustrates a typical mouthwash composition incorporating the salicylamide known as AMCF3-8 and zinc glycinate.

| Mouthwash Ingredient | % Weight |
|---|---|
| Glycerol | 35.00 |
| Ethanol | 27.00 |
| Polyethylene glycol | 10.00 |
| Flavor, color | .90 |
| Zinc glycinate | .25 |
| Polyoxyethylene (20) Sorbitan monolaurate | .20 |
| AMCF3-8 | .2 |
| Water | Balance to 100% |

EXAMPLE 3

The following Example illustrates a further mouthwash composition using the salicylamide known as AN-10 and zinc sulfate.

| Mouthwash Ingredient | % Weight |
|---|---|
| Glycerol | 8.00% |
| Flavor | .15 |
| Saccharin | .02 |
| FD & C Yellow No. 6 (.7% solution) | .10 |
| FD & C Red No. 2 (.2% solution) | .12 |
| AN-10 | .10 |
| Zinc sulfate | .40 |
| Sodium lauryl sulfate | .33 |
| Polyoxyethylene (20) sorbitan monolaurate | .30 |
| Water | Balance to 100% |

EXAMPLE 4

The following Example illustrates a typical gel dentifrice containing zinc phenolsulfonate and the salicylamide AMCF3-8 of this invention.

| Ingredient | % Weight |
|---|---|
| Silica polishing agent[1] | 15.00 |
| Silica polishing agent[2] | 8.00 |
| Sodium carboxymethylcellulose | 0.84 |
| Sorbitol | 36.00 |
| Saccharin | 0.20 |
| Zn phenolsulfonate | 1.00 |
| AMCF3-8 | 0.25 |
| Flavor | 1.30 |
| TiO$_2$ | 0.50 |
| FD & C Blue No. 1 colorant (1% soln.) | 0.02 |
| Sodium Hydroxide | 0.10 |
| Sodium lauryl sulfate-glycerine[3] | 7.00 |
| Water | Balance to 100% |

[1] Syloid 63, a silica xerogel having an average particle diameter of 4-10 microns.
[2] Syloid 244, a silica aerogel having an average particle diameter of 3 microns.
[3] A solution of 21 parts sodium lauryl sulfate in 79 parts glycerol.

Syloid 63 and Syloid 244 are trademarks of the Davison Chemical Division of the W. R. Grace Company.

EXAMPLE 5

The following Example illustrates a high abrasive containing toothpaste utilizing zinc acetate and the salicylamide AN-10 of the present invention.

| Ingredient | % Weight |
|---|---|
| Dicalcium phosphate dihydrate | 40.0 |
| Calcium pyrophosphate | 5.0 |
| Sodium carboxymethylcellulose | 1.0 |
| Glycerol | 20.0 |
| Sorbitol | 10.0 |
| Zinc acetate | 1.5 |
| AN-10 | 0.1 |
| Sodium lauryl sulfate | 1.5 |
| Water | 20.9 |

The foregoing description and Examples illustrate selected embodiments of the present invention and in light thereof various modifications will be suggested to one skilled in the art, all of which are within the spirit and purview of this invention.

What is claimed is:

1. An oral composition comprising:
   (i) from about 0.001 to 10% of a salicylamide of the formula:

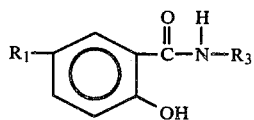

wherein
   (a) $R_1$ is n-decanoyl, and $R_3$ is p-nitrophenyl;
   (b) $R_1$ is n-octanoyl, and $R_3$ is p-trifluoromethylphenyl;
   (c) $R_1$ is n-octanoyl, and $R_3$ is m-trifluoromethylphenyl;
   (d) $R_1$ is n-hexyl, and $R_3$ is p-nitrophenyl;
   (e) $R_1$ is n-butyl, and $R_3$ is m-trifluoromethylphenyl;
   (f) $R_1$ is n-nonanoyl, and $R_3$ is m-carbethoxyphenyl;

(g) $R_1$ is a n-decanoyl, and $R_3$ is benzothiazol-2-yl;
(h) $R_1$ is n-hexadecanoyl, and $R_3$ is thiazol-2-yl; and
(i) $R_1$ is n-decanoyl, the —OH group is replaced by acryloyloxy and $R_3$ is p-nitrophenyl; and
   (ii) from about 0.001 to about 10% of a physiologically acceptable zinc salt.

2. A composition according to claim 1 wherein the salicylamide is present in a concentration from about 0.01 to about 2%.

3. A composition according to claim 1 wherein the salicylamide is present in a concentration from about 0.05 to about 1.5%.

4. A composition according to claim 1 wherein the salicylamide is present in a concentration from about 0.1 to about 1%.

5. A composition according to claim 1 wherein said zinc salt is selected from the group consisting of zinc sulfate, zinc chloride, zinc acetate, zinc phenolsulfonate, zinc borate, zinc bromide, zinc nitrate, zinc glycerophosphate, zinc benzoate, zinc carbonate, zinc citrate, zinc hexafluorosilicate, zinc dllactate trihydrate, zinc oxide, zinc peroxide, zinc salicylate, zinc silicate, zinc soaps of fatty acids having 8–18 carbon atoms, zinc stannate, zinc tannate, zinc tartrate, zinc titanate, zinc tetrafluoroborate, and zinc glycinate.

6. A composition according to claim 1 wherein the concentration of the zinc salt ranges from about 0.05% to about 2%.

7. A composition according to claim 1 further comprising a carrier vehicle selected from the group consisting of water, glycerol, sorbitol and mixtures thereof.

8. A method for controlling plaque on teeth comprising applying to the site of said plaque an effective amount of the composition of claim 7.

* * * * *